United States Patent [19]

Spik et al.

[11] Patent Number: 5,171,845
[45] Date of Patent: Dec. 15, 1992

[54] PROTEIN HOMOLOGUE OF HUMAN ANGIOGENIN

[76] Inventors: Genevieve Spik, 39 Res. du Moulin, Rue de la Marcq en Baroeul; André Tarjar, rue du Moulin, 62490 Vitry-en-Artois; Jean Montreuil, 145 Rue Jules Boucly, 59650 Villeneuve D'Ascq, all of France

[21] Appl. No.: 392,977
[22] PCT Filed: Nov. 18, 1988
[86] PCT No.: PCT/FR88/00566
§ 371 Date: Aug. 21, 1989
§ 102(e) Date: Aug. 21, 1989
[87] PCT Pub. No.: WO89/04837
PCT Pub. Date: Jun. 1, 1989

[30] Foreign Application Priority Data

Nov. 19, 1987 [FR] France .................. 87 15984

[51] Int. Cl.⁵ .......................... C07K 13/00
[52] U.S. Cl. ........................ 530/399; 530/350; 530/806; 530/832; 435/7.9; 436/518; 436/817
[58] Field of Search ............. 530/350, 351, 399, 387, 530/832, 827, 416; 435/7.92

[56] References Cited

U.S. PATENT DOCUMENTS

4,440,860 4/1984 Klagsbrun .................. 435/240.3
4,529,590 7/1985 LeVeen et al. .................. 424/520

OTHER PUBLICATIONS

Yagi ey al., Biol. Abstr. 82(2):12599, 1986.
Bond et al., Biochemistry 27:6282–6287, 1988.
Biochemistry, vol. 24, No. 20, 24 Sep., 1985, pp. 5480–5486, American Chemical Society; J. W. Fett et al.: "Isolation and characterization of angiogenin, an angiogenic protein from human carcinoma cells".
Biochemistry, vol. 24, No. 20, 24 Sep. 1985, pp. 5486–5494, American Chemical Society; D. J. Strydom, et al.: "Amino acid sequence of human tumor derived angiogenin".
Biochemistry, vol. 24, No. 20, 24, Sep. 1985, pp. 5494–5499, American Chemical SOciety K. Kurachi et al.: "Sequence of the cDNA and gene for angiogenin, a human angiogenesis factor".
Biochemistry, vol. 26, No. 16, 11 Aug., 1987, pp. 5141–5146, American Chemical Society; R. Shapiro, et al.: "Isolation of angiogenin from normal human plasma".

*Primary Examiner*—Esther L. Kepplinger
*Assistant Examiner*—Donna C. Wortman
*Attorney, Agent, or Firm*—Oblon, Spivak, McClelland, Maier & Neustadt

[57] ABSTRACT

The invention concerns a new protein of approximately 17 KD, with angiogenic activity, a process for isolating it from mammalian milk, therapeutic compositions containing it, a process for detecting and/or determining the content of mammalian angiogenins, their homologues and their fragments. Said protein, of bovine origin, has a sequence of 125 aminoacids, 81 of which are common to human angiogenin, and a molecular weight of approximately 17 KD, and is extracted from mammalian milk. Application to the detection of mammalian angiogenin.

12 Claims, 1 Drawing Sheet

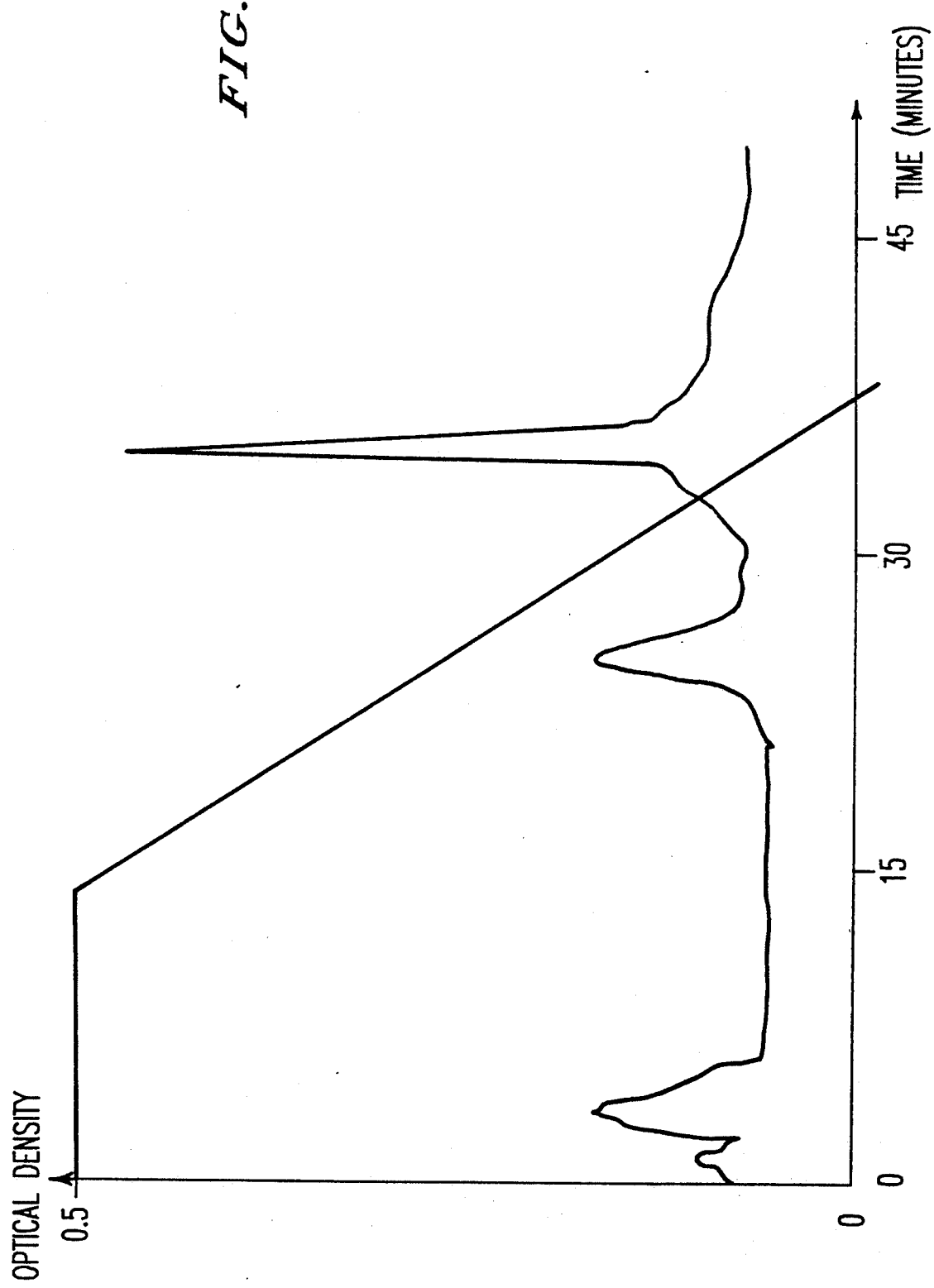

PROTEIN HOMOLOGUE OF HUMAN ANGIOGENIN

The present invention relates to a novel protein of about 17 KD, with angiogenic action, to the method of isolating it from mammalian milk, to therapeutic compositions in which it is present, to a method of detection and/or determination and to immunological reagents for detecting and/or determining mammalian angiogenins, homologs thereof and fragments thereof.

Following the pioneering work of J. FOLKMAN (q.v. J. Exp. Med., 133, 275 (1971)), who demostrated that the growth of a tumor requires a substantial blood supply, this being provided by the continuous growth of new blood vessels, he suggested that this growth results from the presence of a diffusible substance which he called "Tumor Angiogenesis Factor" (TAF). Several proteins which stimulate angiogenesis were isolated (FOLKMAN et al., Science, (1987), 235, 442). Among these substances, angiogenin, a protein of human origin, was purified by VALLEE's team and its gene was cloned. In 1985, J. W. FETT et al. (Biochem., (1985), 24, 5480-5486) isolated human angiogenin from cancerous human intestinal cells in culture. The intestinal cells HT 29 secrete human angiogenin in the culture medium. 0.5 μg/liter of human angiogenin was isolated from these serum-free culture media. VALLEE's team determined the concentration of angiogenin first by Bradford's method (Anal. Biochem., 1975, 72, 248-254, a stain fixing method using SAB as the standard) and then by the method described in Biochem., 1986, 25, 3527-3732, by SHAPIRO et al. The amino acid sequence was also specified by STRYDOM et al. (BIOCHEMISTRY, (1985), 24, p. 5486-5494).

Human angiogenin is a protein with a molecular weight of 14,400 D.

The angiogenin isolated from human tumoral cells consists of a single protein chain comprising 123 amino acids and having the following sequence:

Gln—Asp—Asn—Ser—Arg—Tyr—Thr—His—Phe—Leu—Thr—Gln—

His—Thr—Asp$^{15}$—Ala—Lys—Pro—Gln—Gly—Arg—Asp—Asp—Arg—

Tyr—Cys—Glu—Ser—Ile—Met$^{30}$—Arg—Arg—Arg—Gly—Leu—Thr—

Ser—Pro—Cys—Lys—Arg—Ile—Asn—Thr—Phe$^{45}$—Ile—His—Gly—

Asn—Lys—Arg—Ser—Ile—Lys—Ala—Ile—Cys—Glu—Asn—Lys$^{60}$—

Asn—Gly—Asn—Pro—His—Arg—Glu—Asn—Leu—Arg—Ile—Ser—Lys—

Ser—Ser$^{75}$—Phe—Gln—Val—Thr—Thr—Cys—Lys—Leu—His—Gly—

Gly—Ser—Pro—Trp—Pro$^{90}$—Pro—Cys—Gln—Tyr—Arg—Ala—Thr—

Ala—Gly—Phe—Arg—Asn—Val—Val—Val$^{105}$—Ala—Cys—Glu—Asn—

Gly—Leu—Pro—Val—His—Leu—Asp—Gln—Ser—Ile—Phe$^{120}$—Arg—

Arg—Pro$^{123}$—OH.

The C-terminal amino acid is proline; three disulfide bridges link the cysteines 26-81, 39-92 and 57-107.

The sequence of human angiogenin is 35% homologous with that of human pancreatic ribonuclease, in particular with regard to the amino acids essential for ribonucleolytic activity (q.v. BIOCHEMISTRY, (1985), 24, 5494-5499, KURACHI et al.). The activity of human angiogenin is considerable since 50 ng, i.e. 3.5 picomoles, are capable of causing vascularization of the rabbit cornea and 35 femtomoles are capable of inducing vascularization of the chicken embryo.

It is known to prepare human angiogenin by cloning. Cloning of the gene coding for human angiogenin makes it possible to prepare satisfactory amounts via suitable expression systems. However, such methods are expensive.

It has proved necessary to look for a compound which has properties similar to those of human angiogenin and whose method of preparation is simpler and less expensive.

One object of the present invention is consequently to provide a novel protein which has properties similar to those of human angiogenin and is obtained by inexpensive means which are easy to carry out and afford high quantitative yields.

Another object of the invention is to provide a novel method of obtaining the said protein which does not have the disadvantages of the methods of the prior art; in fact, this novel method makes it possible to obtain large amounts of the protein in question at very low cost, which has important advantages in the context of the industrial manufacture of pharmaceutical compositions containing this protein.

Yet another object of the invention is to provide pharmaceutical compositions containing the said protein.

Another object of the invention is to provide an agent for detecting and determining mammalian angiogenins, homologs thereof and fragments thereof in biological fluids.

Another object of the invention is to provide a kit for detecting and determining the above-mentioned proteins in the said fluids.

The present invention relates to a protein which has a sequence comprising 125 amino acids and has formula I below:

Ala$^1$—Gln—Asp—Asp—Tyr$^5$—Arg—Tyr—Ile—His—Phe$^{10}$— (I)

Leu—Thr—Gln—His—Tyr$^{15}$—Asp—Ala—Lys—Pro—Lys$^{20}$—

Gly—Arg—Asn—Asp—Glu$^{25}$—Tyr—Cys—Phe—Asn—Met$^{30}$—

Met—Lys—Asn—Arg—Arg$^{35}$—Leu—Thr—Arg—Pro—Cys$^{40}$—

Lys—Arg—Arg—Asn—Thr$^{45}$—Phe—Ile—His—Gly—Asn$^{50}$—

-continued

Lys—Asn—Arg—Ile—Lys$^{55}$—Ala—Ile—Cys—Glu—Asp$^{60}$—

Arg—Asn—Gly—Gln—Pro$^{65}$—Tyr—Arg—Gly—Asp—Leu$^{70}$—

Arg—Ile—Ser—Lys—Ser$^{75}$—Glu—Phe—Gln—Ile—Thr$^{80}$—

Ile—Cys—Lys—His—Lys$^{85}$—Gly—Gly—Ser—Ser—Arg$^{90}$—

Pro—Pro—Cys—Arg—Tyr$^{95}$—Gly—Ala—Thr—Glu—Asp$^{100}$—

Ser—Arg—Val—Ile—Val$^{105}$—Val—Gly—Cys—Glu—Asn$^{110}$—

Gly—Leu—Pro—Val—His$^{115}$—Phe—Asp—Glu—Ser—Phe$^{120}$—

Ile—Thr—Pro—Arg—His$^{125}$—OH, whose sequence has 81 amino acids in common with human angiogenin and whose molecular weight is about 17 KD.

The molecular weight was evaluated by comparing the electrophoretic migration speed of the said bovine protein with that of the following references: myoglobin (MW: 17,200), myoglobin 1+2 (MW: 14,600), myoglobin A (MW: 8240), myoglobin 2 (MW: 6380) and myoglobin 3 (MW: 2560) (Pharmacia).

In the composition of the said 17 KD protein, determined after total acid hydrolysis, the following amino acids are present in the proportions given: Phe: 6, Leu: 4, Ile: 9, Met: 2, Val: 4, Pro: 7, Ser: 6, Thr: 6, Ala: 4, Tyr: 6, His: 6, Glu(Gln): 10, Asp(Asn): 16, Lys: 9, Arg: 15, Gly: 9, Cys: 6.

According to the invention, the said protein is obtained by extraction from mammalian milk, especially cow's milk, by cloning or by a synthetic method.

The present invention further relates to peptides which constitute fragments of the 17 KD protein according to the invention; it covers in particular:

- a peptide having the following amino acid sequence:
Glu-Asp$^{60}$-Arg-Asn-Gly-Gln-Pro$^{65}$-Tyr-Arg-Gly-Asp-Leu$^{70}$-Arg-Ile-Ser,
in which 9 out of 15 residues are aligned with the sequence 58-72 of human angiogenin;

- a peptide having the following amino acid sequence:
Phe-Asp-Glu-Ser-Phe$^{120}$-Ile-Thr-Pro-Arg-His$^{125}$,
which corresponds to the C-terminal fragment of the 17 KD protein;

- a peptide having the following amino acid sequence:
Glu-Asn$^{110}$-Gly-Leu-Pro-Val-His$^{115}$-Phe, which is aligned with the sequence 108-115 of human angiogenin, in which sequence 7 out of 8 residues are identical;

- a peptide having the following amino acid sequence:
Ile-Val$^{105}$-Val-Gly-Cys-Glu,
in which 4 out of 6 residues are aligned with the sequence 103-108 of human angiogenin;

- a peptide having the following amino acid sequence:
Arg-Tyr-Ile-His-Phe$^{10}$-Leu-Thr-Gln-His-Tyr$^{15}$-Asp-Ala-Lys,
in which 11 out of 13 residues are aligned with the sequence 5-17 of human angiogenin;

- a peptide having the following amino acid sequence:
Asn-Thr$^{45}$-Phe-Ile-His-Gly-Asn$^{50}$-Lys,
which is distinguished by total homology with the sequence 43-50 of human angiogenin;

- a peptide having the following amino acid sequence:
Ile-Lys$^{55}$-Ala-Ile-Cys-Glu,
which is also distinguished by total homology with the sequence 53-58 of human angiogenin;

- a peptide having the following amino acid sequence:
Leu$^{70}$-Arg-Ile-Ser-Lys-Ser$^{75}$-Glu-Phe-Gln,
in which 8 out of 10 residues are aligned with the sequence 69-77 of human angiogenin; and

- a peptide having the following amino acid sequence:
Arg$^{67}$-Gly-Asp,
the said peptide being recognized by an endothelial cell receptor.

The present invention further relates to a method of obtaining the said protein according to the invention, wherein the said protein is extracted from mammalian milk, especially cow's milk.

In an advantageous way of carrying out the method according to the invention, the said protein is extracted by cation exchange chromatography followed by elution with an appropriate eluent.

According to an advantageous provision of this way of carrying out the method, the eluent is an alkali metal salt of a weak organic acid, especially sodium acetate.

According to another advantageous provision, the eluted fraction is subjected to cation exchange chromatography a second time.

The protein isolated in this manner is purified by chromatography on a gel filtration column.

The protein purified in this manner is obtained with a yield of the order of 0.5 mg/liter of milk.

As a variant of this way of carrying out the method, the milk of bovine origin is subjected to delipidation prior to extraction.

According to an advantageous provision, delipidation is effected by centrifugation.

In an advantageous modification of this provision, centrifugation is carried out at 4000 g for 30 min at a temperature of 4° C.

The present invention further relates to a therapeutic composition which comprises, as the active compound, the 17 KD protein and/or fragments or homologs thereof, especially for the treatment of disorders which require the growth of blood vessels to be inhibited or increased.

The therapeutic compositions according to the invention can be used in all pathologies in which there is a problem of vascularization, and especially wounds, scabs, ulcers, grafts and circulatory insufficiencies. They can also be used in cosmetology (skin, scalp). They can also be used in the field of veterinary medicine, especially in the diagnosis of mastitis and the selection of milking cows.

The present invention further relates to an immunological reagent for detecting or determining mammalian angiogenins which is selected from the group comprising antibodies directed against the 17 KD protein and antipeptide antibodies, especially antibodies directed against one of the peptides defined above, the said antibodies being used by themselves or in a mixture.

The present invention further relates to a method of detecting and determining mammalian angiogenins in biological fluids, wherein an anti-angiogenin antibody, especially an antibody directed against the 17 KD protein or an anti-peptide antibody, according to the invention, is reacted, under appropriate conditions, with a biological fluid thought to contain the said angiogenin, the reaction being evaluated by an appropriate means such as, in particular, RIA, ELISA or immunofluorescence.

The present invention further relates to a kit for detecting and/or determining mammalian angiogenin, and especially human angiogenin, in biological fluids, which comprises:

an appropriate amount, subdivided into unit doses if necessary, of anti-angiogenin antibodies, in particular antibodies directed against the 17 KD protein or antipeptides antibodies, especially antibodies directed against one of the peptides defined above; and if necessary, an appropriate amount of buffers, diluents and reagents required to carry out the said detection and/or determination.

In addition to the foregoing provisions, the invention also includes other provisions which will become apparent from the following description referring to an Example of the preparation of the protein according to the invention and to an account of experiments performed:

to demonstrate the homology between human angiogenin and the 17 KD protein of bovine origin, according to the invention;

to demonstrate the homology with ribonuclease; and to demonstrate the activity of the said 17 KD protein of bovine origin on angiogenesis.

It must be clearly understood, however, that these Examples and this account of experiments are given solely in order to illustrate the subject of the invention, without in any way implying a limitation.

"Sephadex" ®, "Sepharose" ®, "Biogel" ® and "Phenyl Superose" ® are well known trademarks in the field of chromatography. "Sephadex" and "Sepharose" are dextran polymers on which anionic or cationic functions have been grafted. "Phenyl Superose" ® corresponds to cross-linked agarose. "Biogel P gels" are porous polyacrylamide beads prepared by copolymerization of acrylamide and N,N'-methylene-bis-acrylamide.

BRIEF DESCRIPTION OF THE DRAWING

FIG. 1 shows the diagram of the elution of the 17 KD protein from the Phenyl Superose column, the time in minutes being plotted on the abscissa and the optical densities on the ordinate. Peak 2 contains the pure 17 KD protein.

EXAMPLE A: Extraction of the 17 KD Protein from Cow's Milk 50 liters of cow's milk are delipidated by centrifugation (4000×g-30 min-4° C.) and chromatographed on a column of SP-Sephadex C50 (10×100 cm) (Pharmacia).

The column is washed with 10 l of a 0.35M solution of sodium acetate, pH 7, and then eluted with 5 l of 1.5M sodium acetate, pH 8. The solution obtained is diluted to give a sodium acetate concentration of 0.2M. This solution is chromatographed on a column of S-Sepharose Fast Flow (10×100 cm) (Pharmacia) which has been equilibrated beforehand with 0.22M sodium acetate, pH 6.5. After the column has been washed with the same acetate solution, the protein is eluted with one liter of a 0.4M solution of sodium acetate.

Salt is removed from this solution by gel filtration chromatography on a column of Bio-gel P-30 (4×100 cm).

After the column has been eluted with water, the fraction containing the protein in chromatographed on a column of Phenyl Superose HR5/5 (Pharmacia) by FPLC (Fast Protein Liquid Chromatography). Elution is performed using a gradient obtained by mixing buffer A-50 mM sodium phosphate, 1.7M ammonium sulfate, pH 7-with buffer B-50 mM sodium phosphate, pH 7 (time 0 minute: 100% buffer A; time 15 minutes: 100% buffer A; time 40 minutes: 0% buffer A).

FIG. 1 attached shows the diagram of the elution of the 17 KD protein from the Phenyl Superose column, the time in minutes being plotted on the abscissa and the optical densities on the ordinate. Peak 2 contains the pure 17 KD protein. The yield is 25 mg of protein, i.e. 0.5 mg/l of delipidated milk.

TESTS

EXAMPLE 1: Homology Between Human Angiogenin and the 17 KD Protein

The data which we have available on the 17 KD protein show its relationship with human angiogenin; in fact, 81 amino acids are common to both proteins.

Amino acid analysis, evaluated for human angiogenin and determined after total acid hydrolysis for the 17 KD protein of bovine origin (Table I below), shows that the two proteins have very similar compositions.

TABLE I

| COMPARATIVE AMINO ACID ANALYSIS OF HUMAN ANGIOGENIN AND THE 17 KD PROTEIN OF BOVINE ORIGIN | | |
|---|---|---|
| | HU | BO |
| Phe | 5 | 6 |
| Leu | 6 | 4 |
| Ile | 7 | 9 |
| Met | 1 | 2 |
| Val | 5 | 4 |
| Pro | 8 | 7 |
| Ser | 9 | 6 |
| Thr | 8 | 6 |
| Ala | 5 | 4 |
| Tyr | 3 | 6 |
| His | 6 | 6 |
| Glu(Gln) | 10 | 10 |
| Asp(Asn) | 14 | 16 |
| Lys | 7 | 9 |
| Cys | 6 | 6 |
| Trp | 1 | — |
| Arg | 14 | 15 |
| Gly | 8 | 9 |
| Total* | 116 | 119 |

*without Cys and Trp

The comparison of the sequences of human angiogenin and the 17 KD protein of bovine origin which is given in Table II below shows a homology of more than 60%. Most of the differences are the result of conservative substitutions.

The 6 cysteine residues are in the same position, which indicates a tertiary structure similar to that of human angiogenin, a single shift being necessary in the C-terminal region for alignment; only the N- and C-terminal regions are responsible for the difference in size between the two proteins (the 17 KD protein has two amino acids more than human angiogenin).

However, as distinct from human angiogenin, which has a pyroglutamic acid in the N-terminal position, the 17 KD protein of bovine origin has an additional alanine in the N-terminal position.

This difference is explained by the presence of a signal peptide of 24 (or 22) amino acids (J. FETT et al., Biochem., (1985), 24, 5480), revealed by sequencing of the cDNA's coding for human angiogenin; suppression of this peptide takes place on treatment with the signal peptidase, which cleaves between the alanine and the glutamine in: Pro-Pro-Thr-Leu-Ala$-^1$-Glu$+^1$-Asp-Asn. . . , in human angiogenin, whereas the presence of the N-terminal alanine in the 17 KD protein of bovine origin is due to displacement of the linkage cleaved by the signal peptidase, thereby leaving an additional alanine in the N-terminal position and avoiding the modification to pyroglutamic acid which is observed in the case of human angiogenin.

The sequence of the 17 KD protein, as shown in Table II below, was determined by the conventional protein sequencing techniques.

Except for the Arg/Ile mutation in position 43 and two conservative substitutions (Asp-69 for Asn-68 and Phe-116 for Leu-115), all the residues which are known to be involved in the ribonucleolytic activity are preserved, both in human angiogenin and in the 17 KD protein of bovine origin, indicating a strong selection pressure for maintaining this significant functional homology (Table III).

TABLE II

COMPARATIVE SEQUENCES OF THE 17 KD PROTEIN AND ANGIOGENIN

```
                    1           5              10                    15                    20
17 KD protein    Ala  Gln Asp  Asp Tyr  Arg Tyr  Ile  His Phe Leu Thr Gln His  Tyr  Asp Ala Lys Pro  Lys  Gly Arg  Asn  Asp
Human                 Gln Asp  Asn Ser  Arg Tyr  Thr  His Phe Leu Thr Gln His  Thr  Asp Ala Lys Pro  Gln  Gly Arg  Asp  Asp
angiogenin 25              30                  35                    40
17 KD protein         Glu  Tyr Cys  Phe Asn Met  Met  Lys Asn  Arg  Arg  Leu Thr  Arg  Pro Cys Lys Asp  Arg
Human angiogenin      Arg  Tyr Cys  Glu Ser Ile  Met  Arg Arg  Arg  Gly  Leu Thr  Ser  Pro Cys Lys Asp  Ile 45                      50                      55                      60                65
17 KD protein         Asn Thr Phe Ile His Gly Asn Lys  Asn Asp  Ile Lys Ala Ile Cys Glu  Asp Arg  Asn Gly  Gln  Pro  Tyr  Arg
Human angiogenin      Asn Thr Phe Ile His Gly Asn Lys  Arg Ser  Ile Lys Ala Ile Cys Glu  Asn Lys  Asn Gly  Asn  Pro  His  Arg 70               75            80                   85                    90
17 KD protein         Gly Asp  Leu   Arg Ile Ser Lys Ser   Glu  Phe Gln  Ile  Thr  Ile  Cys Lys  His Lys  Gly Gly Ser   Ser Arg
Human angiogenin      Glu Asn  Leu   Arg Ile Ser Lys Ser   Ser  Phe Gln  Val  Thr  Thr  Cys Lys  Leu His  Gly Gly Ser   Pro Trp 95             100             105              110                       115
17 KD     Pro Pro Cys  Arg  Tyr  Gly  Ala Thr  Glu Asp Ser  Arg  Val Ile  Val  Val  Gly  Cys Glu Asn Gly Leu Pro Val His
protein   Pro Pro Cys       Gln  Tyr  Arg  Ala Thr  Ala Gly Phe  Arg  Asn Val  Val  Val  Ala  Cys Glu Asn Gly Leu Pro Val His
Human
angiogenin 120             125
         Phe  Asp  Glu  Ser   Phe Ile Thr Pro Arg His
         Leu  Asp  Gln  Ser   Ile Phe Arg Arg Pro
```

EXAMPLE 2-Homology with RNase

R. SHAPIRO et al. (Biochem., (1986), 25, 3527-3532) showed that, in practice, all the residues of the sequence of the active site of bovine RNase are preserved in human angiogenin.

Furthermore, the observation that a human ribonuclease inhibitor suppresses both the angiogenic and the ribonucleolytic activity of human angiogenin confirms that the homology of angiogenin with RNase is functionally significant.

The following results confirm these observations (Table III below):

The homology of the 17 KD protein of bovine origin with bovine RNase (39% of the residues being identical) is similar to that of human angiogenin with human RNase (34% of the residues being identical).

The substitution of Phe-116 of the 17 KD protein of bovine origin for Leu-115 of human angiogenin is of particular interest: it has been shown, for example, that the replacement of Phe by Leu in RNase causes the activity to drop by a factor of 10. Thus, subject to the RNase activity being directly involved in its biological activity, the presence of Phe-116 in the 17 KD protein could be an indication of a greater activity than that of human angiogenin.

Based on its homology with pancreatic ribonuclease A, the three-dimensional structure of human angiogenin was evaluated when the sites affected by the mutations are reincorporated into this structure; in this case, it can be observed that, with the exception of the Arg/Ile mutation in position 43, all the substitutions occurring in the three-dimensional structure of the protein which are involved in its ribonucleolytic activity are conservative substitutions.

TABLE III

HOMOLOGIES BETWEEN HUMAN ANGIOGENIN AND THE 17 KD PROTEIN
AND BETWEEN BOVINE AND HUMAN RNases

```
Bovine RNase          K E T  A A A K F E R Q H M D S S T  S  A A S S S  N Y C  N Q  M M K S
17 KD protein      A  Q D D Y  R Y I H F L T Q H Y D A K P  K  G R N D E  — Y C  F N  M M K N
Human angiogenin   <  Q D N S  R Y T H F L T Q H Y D A K P  Q  G R D D R  — Y C  E S  I M R R
Human RNase           K E S  R A K K F Q R Q H M D S D S  S  P S S S S  T Y C  N Q  M M R R Bovine RNase       R N L T K   D R C K P V  N T F V H E S L  A  D V Q A V C S Q K N V A
17 KD protein      R N L T K   D R C K P V  N T F V H E S L  A  D V Q A V C S Q K N V A
Human angiogenin   R R L T R   P — C K D R  N T F I H G N K N  D I K A I C E D R N G Q
Human RNase        R G L T S   P — C K D I  N T F I H G N K R  S I K A I C E N K N G N
                   R N M I Q  G R C K P V  N T F V H E P L  V  D V Q N V C F Q H K V T
```

TABLE III-continued

HOMOLOGIES BETWEEN HUMAN ANGIOGENIN AND THE 17 KD PROTEIN
AND BETWEEN BOVINE AND HUMAN RNases

```
Bovine RNase    C K N G Q T  N C Y Q S Y S T M S I T D  C R E T G S S K Y  P N C A
17 KD protein   P Y R G – – D L R I S K S E F Q I T I  C K H K G G S S R  P P C R
Human angiogenin P H R E – – N L R I S K S S F Q V T T C K L H G G S P W  P P C Q
Human RNase     C K N G Q G N C Y K S N S S M H I T D  C R L T N G S R Y  P N C A Bovine RNase    Y K T T Q A N K H I I V A  C E G N P Y V P V H F D A S V
17 KD protein   Y G A T E D S R V L V V G  C E – N G – L P V H F D E S F I T P R M
Human angiogenin Y R A T A G F R N V V V A C E – N G – L P V H L D Q S I F R R P
Human RNase     Y R T S P K E R H I I V A  C E G S P Y V P V H F D A S V E D S
```

EXAMPLE 3-BIOLOGICAL PROPERTIES OF THE 17 KD PROTEIN OF BOVINE ORIGIN

-Chicken egg chorioallantoic membrane test:

This test of biological activity has been described by FETT et al. (Biochem., (1985), 24, 5480-5486). It consists in assessing the development of blood vessels in the chorioallantoic membrane of the chicken embryo after the application of increasing amounts, of the order of 10 ng to 1 μg, of the 17 KD protein of bovine origin. Out of 80 fertilized eggs which were investigated in the presence of the 17 KD protein, the development of new blood vessels was observed in 62 eggs for an amount of 50 ng of angiogenin. These results show that the 17 KD protein according to the invention has an effect on organogenesis and the growth of blood vessels.

The fertilized eggs are placed in an incubator at 38° C. in an atmosphere of 70% humidity.

After 3 days, an aperture is made in the shell and sealed with a gas-permeable membrane.

On day 5, a disk of a membrane soaked with a solution of the 17 KD protein is implanted on the chorioallantoic membrane.

The development of the blood vessels which converge towards the disk soaked with angiogenin is followed on days 8, 9 and 10 using binoculars.

The 17 KD protein of bovine origin according to the invention can be used in a pharmaceutically acceptable form for the treatment of disorders which require the growth of blood vessels in man to be inhibited or increased.

As is apparent from the foregoing description, the invention is in no way limited to those embodiments and methods of application which have now been explicitly described; on the contrary, it encompasses all the variants thereof which may occur to those skilled in the art, without deviating from the framework or the scope of the present invention.

What is claimed is:

1. An isolated and purified protein which has a sequence comprising 125 amino acids and has formula I below:

Ala$^1$—Gln—Asp—Asp—Tyr$^5$—Arg—Tyr—Ile—His—Phe$^{10}$— (I)

Leu—Thr—Gln—His—Tyr$^{15}$—Asp—Ala—Lys—Pro—Lys$^{20}$—

Gly—Arg—Asn—Asp—Glu$^{25}$—Tyr—Cys—Phe—Asn—Met$^{30}$—

Met—Lys—Asn—Arg—Arg$^{35}$—Leu—Thr—Arg—Pro—Cys$^{40}$—

Lys—Arg—Arg—Asn—Thr$^{45}$—Phe—Ile—His—Gly—Asn$^{50}$—

Lys—Asn—Arg—Ile—Lys$^{55}$—Ala—Ile—Cys—Glu—Asp$^{60}$—

Arg—Asn—Gly—Gln—Pro$^{65}$—Tyr—Arg—Gly—Asp—Leu$^{70}$—

Arg—Ile—Ser—Lys—Ser$^{75}$—Glu—Phe—Gln—Ile—Thr$^{80}$—

Ile—Cys—Lys—His—Lys$^{85}$—Gly—Gly—Ser—Ser—Arg$^{90}$—

Pro—Pro—Cys—Arg—Tyr$^{95}$—Gly—Ala—Thr—Glu—Asp$^{100}$—

Ser—Arg—Val—Ile—Val$^{105}$—Val—Gly—Cys—Glu—Asn$^{110}$—

Gly—Leu—Pro—Val—His$^{115}$—Phe—Asp—Glu—Ser—Phe$^{120}$—

Ile—Thr—Pro—Arg—His$^{125}$—OH, whose sequence has 81 amino acids in common with human angiogenin and whose molecular weight is about 17 KD.

2. A method of obtaining the protein according to claim 1 comprising: extracting cow's milk and recovering said protein.

3. The method according to claim 2 wherein the product obtained is purified by chromatography on a gel filtration column.

4. The method according to claim 2 wherein the milk is first delipidated by centrifugation.

5. The method according to claim 2 wherein extraction is carried out by cation exchange chromatography followed by elution with an appropriate eluent.

6. The method according to claim 5 wherein the product obtained is purified by chromatography on a gel filtration column.

7. The method according to claim 5 wherein the eluent contains sodium acetate or another alkali metal salt of a weak organic acid.

8. The method according to claim 5 or 7 wherein the eluted fraction is subjected to cation exchange chromatography a second time, followed by elution with an appropriate eluent a second time.

9. The method according to claim 8 wherein the product obtained is purified by chromatography on a gel filtration column.

10. The method according to claim 8 wherein the eluent contains sodium acetate or another alkali metal salt of a weak organic acid.

11. The method according to claim 10 wherein the product obtained is purified by chromatography on a gel filtration column.

12. The method according to claim 7 wherein the product obtained is purified by chromatography on a gel filtration column.

* * * * *

UNITED STATES PATENT AND TRADEMARK OFFICE
CERTIFICATE OF CORRECTION

PATENT NO. : 5,171,845
DATED : December 15, 1992
INVENTOR(S) : Genevieve Spik et al.

It is certified that error appears in the above-identified patent and that said Letters Patent is hereby corrected as shown below:

On the title page, Item [73],

The assignee has been omitted, should read as follows:

--CENTRE NATIONAL DE LA RECHERCHE SCIENTIFIQUE-CNRS, Paris; INSTITUT PASTEUR DE LILLE, Lille; INSTITUT PASTEUR, Paris Cedex, all of FRANCE--

Signed and Sealed this

Thirtieth Day of November, 1993

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,171,845

DATED : December 15, 1992

INVENTOR(S) : Genevieve Spik, et al.

It is certified that error appears in the above-identified patent and that said Letters Patent is hereby corrected as shown below:

On the title page item (75) inventors: The second inventor's last name should read --Tartar--.

Signed and Sealed this

Twenty-second Day of February, 1994

Attest:

BRUCE LEHMAN

*Attesting Officer*    *Commissioner of Patents and Trademarks*